US010000732B2

(12) United States Patent
Hsu et al.

(10) Patent No.: US 10,000,732 B2
(45) Date of Patent: Jun. 19, 2018

(54) MICROFLUIDIC DUAL-WELL DEVICE FOR HIGHTHROUGHPUT SINGLE-CELL CAPTURE AND CULTURE

(71) Applicant: NATIONAL HEALTH RESEARCH INSTITUTES, Miaoli County (TW)

(72) Inventors: Chia-Hsien Hsu, Miaoli County (TW); Ching-Hui Lin, Miaoli County (TW); Hao-Chen Chang, Miaoli County (TW); Ing-Ming Chiu, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 93 days.

(21) Appl. No.: 15/159,712

(22) Filed: May 19, 2016

(65) Prior Publication Data
US 2017/0145363 A1 May 25, 2017

Related U.S. Application Data

(60) Provisional application No. 62/258,174, filed on Nov. 20, 2015.

(51) Int. Cl.
C12M 3/06 (2006.01)
B01L 3/00 (2006.01)
(Continued)

(52) U.S. Cl.
CPC ....... C12M 23/16 (2013.01); B01L 3/502707 (2013.01); B01L 3/502715 (2013.01);
(Continued)

(58) Field of Classification Search
CPC ...... C12M 23/16; C12M 23/50; C12M 23/12; B01L 3/502715; B01L 3/502761;
(Continued)

(56) References Cited

U.S. PATENT DOCUMENTS

2003/0148401 A1* 8/2003 Agrawal et al. ..... B01J 19/0046
506/9

OTHER PUBLICATIONS

Lin et al. "A microfluidic dual-well device for highthroughput single-cell capture and culture" Lab Chip, 2015, 15, 2928-2938.

* cited by examiner

Primary Examiner — Gautam Prakash
(74) Attorney, Agent, or Firm — Hsiu-Ming Saunders; Intellectual Property Connections, Inc.

(57) ABSTRACT

A microfluidic dual-well device is disclosed. The device comprises: (a) a first substrate having a first end, a second end, and a culture microwell forming portion; (b) a plurality of culture microwells; (c) a second substrate having a first end, a second end, and a capture microwell forming portion, the two ends of the second substrate being respectively bounded to the two ends of the first substrate; (d) a plurality of capture microwells; (e) a microfluidic channel; (f) a microfluidic inlet port; and (g) a microfluidic outlet port; wherein the microfluidic channel is in fluidic connections with the culture microwells, the capture microwells, and the inlet and outlet ports. Methods of capturing and transferring a single cell or a single cell colony for culture, and method of transferring a target cell from a polydimethylsiloxane (PDMS) structure of culture microwells to a culture plate for culture are also disclosed.

18 Claims, 11 Drawing Sheets

(51) Int. Cl.
*C12M 1/00* (2006.01)
*C12M 1/32* (2006.01)
*C12M 1/26* (2006.01)

(52) U.S. Cl.
CPC ....... *B01L 3/502761* (2013.01); *C12M 23/12* (2013.01); *C12M 23/50* (2013.01); *C12M 33/00* (2013.01); *B01L 2200/0647* (2013.01); *B01L 2300/0829* (2013.01); *B01L 2300/0887* (2013.01); *B01L 2300/12* (2013.01); *B01L 2300/16* (2013.01)

(58) Field of Classification Search
CPC ....... B01L 3/502707; B01L 2300/0887; B01L 2300/0829; B01L 2300/16; B01L 2200/0647; B01L 2300/12
See application file for complete search history.

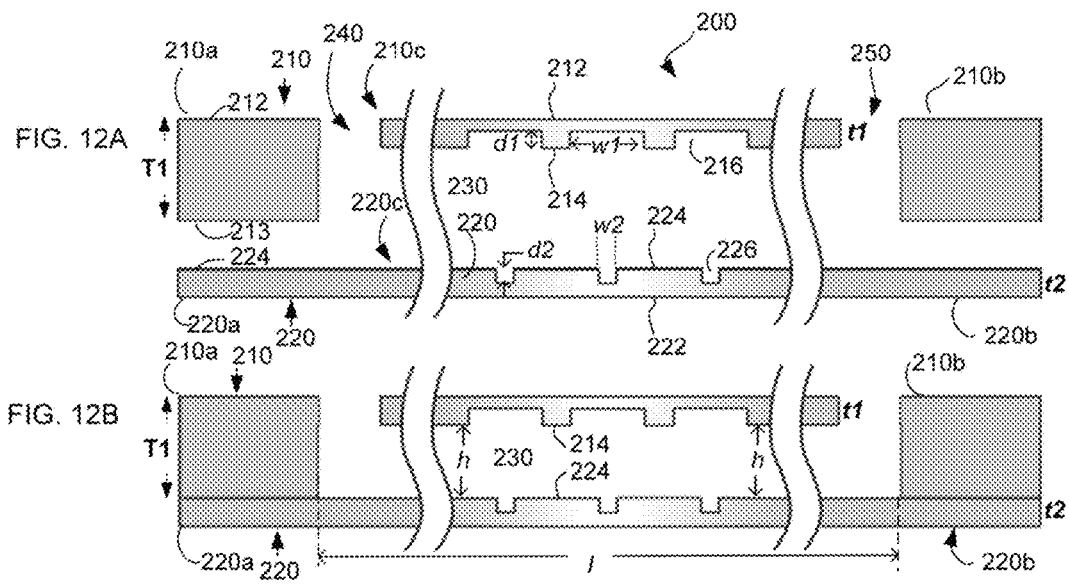
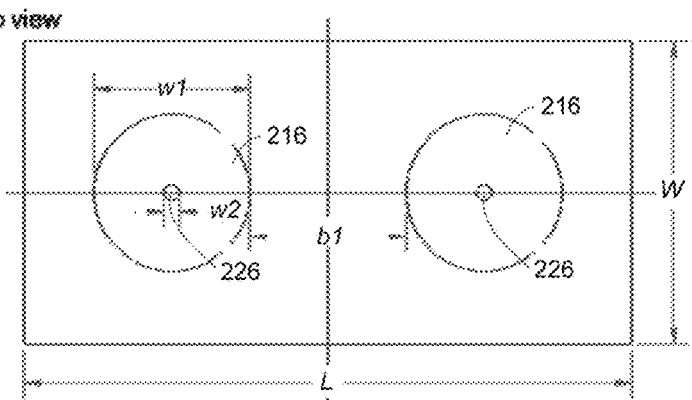

MICROFLUIDIC DUAL-WELL DEVICE FOR HIGHTHROUGHPUT SINGLE-CELL CAPTURE AND CULTURE

REFERENCE TO RELATED APPLICATION

The present application claims the priority to U.S. Provisional Application Ser. No. 62/258,174, filed Nov. 20, 2015, which is herein incorporated by reference in its entirety.

FIELD OF THE INVENTION

The present invention relates generally to a biological microfluidic chip and more specifically to a biological microfluidic chip for single-cell capture and culture.

BACKGROUND OF THE INVENTION

Analyzing individual cells is technically more challenging compared to measuring the averaged outcome from a cell population. Such tasks are commonly performed with limiting dilution or fluorescence-activated cell sorting (FACS). Limiting dilution is based on placing diluted cell suspension in culture wells (e.g., plastic well plates) to obtain one-cell-in-a-well events, and is widely used for single cell assays such as colony formation of cancer stem/initiating cells. This method is convenient but low-throughput without using pipetting robot because the maximum probability of single-cell event is under 37% according to the Poisson distribution.

FACS can overcome the Poisson distribution limitation and provide an alternative method to efficiently obtain single-cell events by sorting and placing individual cells in well plates. However, the high mechanical shear stress in FACS can damage cells and affect their downstream uses. In addition, FACS is less prevalent in many laboratories due to its high machine-purchasing and operational cost.

Microfabricated devices have been utilized for capturing single cells for single cell analysis using microdroplets, dielectrophoresis, hydrodynamics, selective dewetting, mechanical techniques and microwell array on different substrates. For cell-based applications that require culturing single cells, microdroplet-based methods represent a powerful means of obtaining larger numbers of microdroplets each containing a single cell. However it is difficult to change the medium inside the microdroplets, making it not suitable for applications where the initial medium need to be replaced during experiment. In addition cells encapsulated in microdroplets are not suitable for adherent cell culture due to the lack of a substrate for cell to attach and spread.

On the other hand, trapping single cells in microwells is an attractive method to set up larger numbers of single cells for both adherent and suspension single-cell cultures due to its simplicity in device fabrication and operation as they only require physical walls and simple manipulation to load cells in compartmented spaces for subsequent culture and analysis. However, to provide a sufficient space for cell growth, the sizes of the microwells had to be made much larger (from 90-650 µm in diameter or in side length) than that of a single cell, resulting in low single-cell events (ranging from 10-30%). The decreased single-cell-loading efficiency in culture microwells is due to the inherent limitation of the Poisson distribution also seen in conventional limiting dilution method. This limitation was improved by using triangle-shaped microwells which were able to provide enlarged area for cell growth while maintain good single-cell loading efficiency (up to about 58%). However the enlarged area (about 3.5-6 times of that of a single cell) in a microwell was insufficient for cell growth beyond two days. There is still a lack of simple yet high-throughput method and device to perform single cell culture experiment.

SUMMARY OF THE INVENTION

In one aspect, the invention relates to a microfluidic dual-well device comprising: (a) a first substrate, having a first end, a second end opposite to the first end, and a culture microwell forming portion with a thickness of t1 located between the two ends, each end having a first surface and a second surface and a thickness of T1, the culture microwell forming portion having a first surface and a second surface opposite to the first surface, wherein the thickness T1 of each end of the first substrate is greater than the thickness t1 of the culture microwell forming portion; (b) a plurality of culture microwells, each microwell having a diameter of w1 and a depth of d1, extending from the second surface toward the first surface of the culture microwell forming portion; (c) a second substrate with a thickness of t2, having a first surface and a second surface opposite to the first surface of the second substrate, the second substrate having a first end, a second end opposite to the first end, and a capture microwell forming portion located between the two ends of the second substrate, the two ends of the second substrate being respectively bounded to the two ends of the first substrate with its second surface facing toward the second surface of the first substrate at a distance of h; (d) a plurality of capture microwells, each microwell having a diameter of w2 and a depth of d2, extending from the second surface toward the first surface of the second substrate, wherein the capture microwells are in alignment with the culture microwells so that each microwell is corresponding to one culture microwell and the projected area of each capture microwell is within the projected area of the corresponding culture well, wherein the diameter w2 of each capture microwell is smaller than the diameter w1 of each culture microwells; (e) a microfluidic channel with a length of l, a width of w3 and a height of h, formed between the two second surfaces of culture and capture microwell forming portions; (f) a microfluidic inlet port defining an opening in the first surface of the first substrate; and (g) a microfluidic outlet port defining an opening in the first surface of the first substrate, opposite to the microfluidic inlet port; wherein the microfluidic channel is in fluidic connections with the culture microwells, the capture microwells, and the inlet and outlet ports.

In one embodiment of the invention, the surfaces of the microfluidic channel are coated with albumin.

In another embodiment of the invention, the surfaces of the microfluidic channel are coated with bovine serum albumin.

Further in another embodiment of the invention, the microfluidic dual-well device of the invention further comprises a fitting adapted to seal the inlet and outlet ports.

Further in another embodiment of the invention, the inlet and outlet ports are scaled liquid-tight.

Further in another embodiment of the invention, the microfluidic dual-well device of the invention further comprises cells suspended in a medium within the microfluidic channel, wherein the size of each well of the capture microwells is adapted to capture a single cell from the cells within the microfluidic channel.

Further in another embodiment of the invention, the microfluidic dual-well device of the invention further comprises single cells in the capture microwells.

Further in another embodiment of the invention, the microfluidic dual-well device of the invention further comprises single cells in the culture microwells.

Further in another embodiment of the invention, more than one well of the culture microwells comprise a single cell, and each well of the culture microwells has space adapted for the single cell to attach, grow and/or proliferate.

Further in another embodiment of the invention, more than one well of the culture microwells comprise a single-cell colony.

Further in another embodiment of the invention, the microfluidic dual-well device of the invention further comprises a tubing adapted to connect to the inlet and/or outlet ports.

Further in another embodiment of the invention, each well of the capture microwells has a depth of no greater than 30 μm.

Further in another embodiment of the invention, each well of the capture microwells has a depth of less than 30 μm.

Further in another embodiment of the invention, the first and second substrates are made of a material selected from the group consisting of polydimethylsiloxane (PDMS), polymethyl methacrylate (PMMA), and polycarbonate (PC).

In another aspect, the invention relates to a method of capturing and transferring a single cell or a single cell colony for culture, comprising: (a) providing the microfluidic dual-well device of the invention with the first substrate on the top and the second substrate at the bottom; (b) loading cells suspended in a culture medium into the microfluidic channel via the inlet port; (c) allowing the cells in the microfluidic channel to settle into and captured by the capture microwells and/or to settle on the second surface of the second substrate; (d) washing away uncaptured cells by delivering a washing medium into the microfluidic channel via the inlet port; and (e) flipping over the microfluidic dual-well device to place the first substrate at the bottom and the second substrate on the top to transfer the captured cells from the capture microwells to the culture microwells for culture.

In one embodiment of the invention, the aforementioned step (c) further comprises the step of: sweeping the cells settled on the second surface of the second substrate by delivering the culture medium into the microfluidic channel to increase the probability of cell docking in the capture microwells, wherein the flow rate of the medium during the sweeping step is slower than that during the washing step.

In another embodiment of the invention, the method further comprises: (f) separating the first substrate from the second substrate; (g) punching out one portion of the first substrate encompassing a culture microwell containing a captured cell to obtain a substrate plug containing the captured cell, wherein each culture microwell containing the captured cell is punched out one well at a time; (h) transferring the substrate plug containing the captured cell into a well of a culture plate containing a dissociation solution; and (i) releasing the captured cell from the substrate plug to obtain a single cell for culture.

Further in another embodiment of the invention, the culture microwell in the aforementioned step (g) contains a single cell colony.

Further in another aspect, the invention relates to a method of transferring a target cell from a polydimethylsiloxane (PDMS) structure of culture microwells to a culture plate, comprising: (a) providing the PDMS structure of culture microwells containing the target cell attached to the bottom of the well of the culture microwells; (b) punching out one portion of the PDMS structure encompassing the target cell to obtain a PDMS plug or a PDMS piece containing the target cell, wherein the target cell is punched out one well at a time; (c) transferring the PDMS plug or piece containing the target cell into a well of a culture plate containing a dissociation solution; and (d) releasing the target cell from the PDMS plug to obtain a single cell in the culture plate for culture.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 12A-D are schematic drawings illustrating a dual-well (DW) device according to one embodiment of the invention. (A) a cross section view showing the first substrate and the second substrate are separate. (B) a cross section view showing the first substrate and the second substrate are assembled and bonded together. (C) a top view showing culture microwells and capture microwells. (D) a cross section view showing culture and capture microwells and microfluidic channel.

DETAILED DESCRIPTION OF THE INVENTION

Definitions

Figure 1:
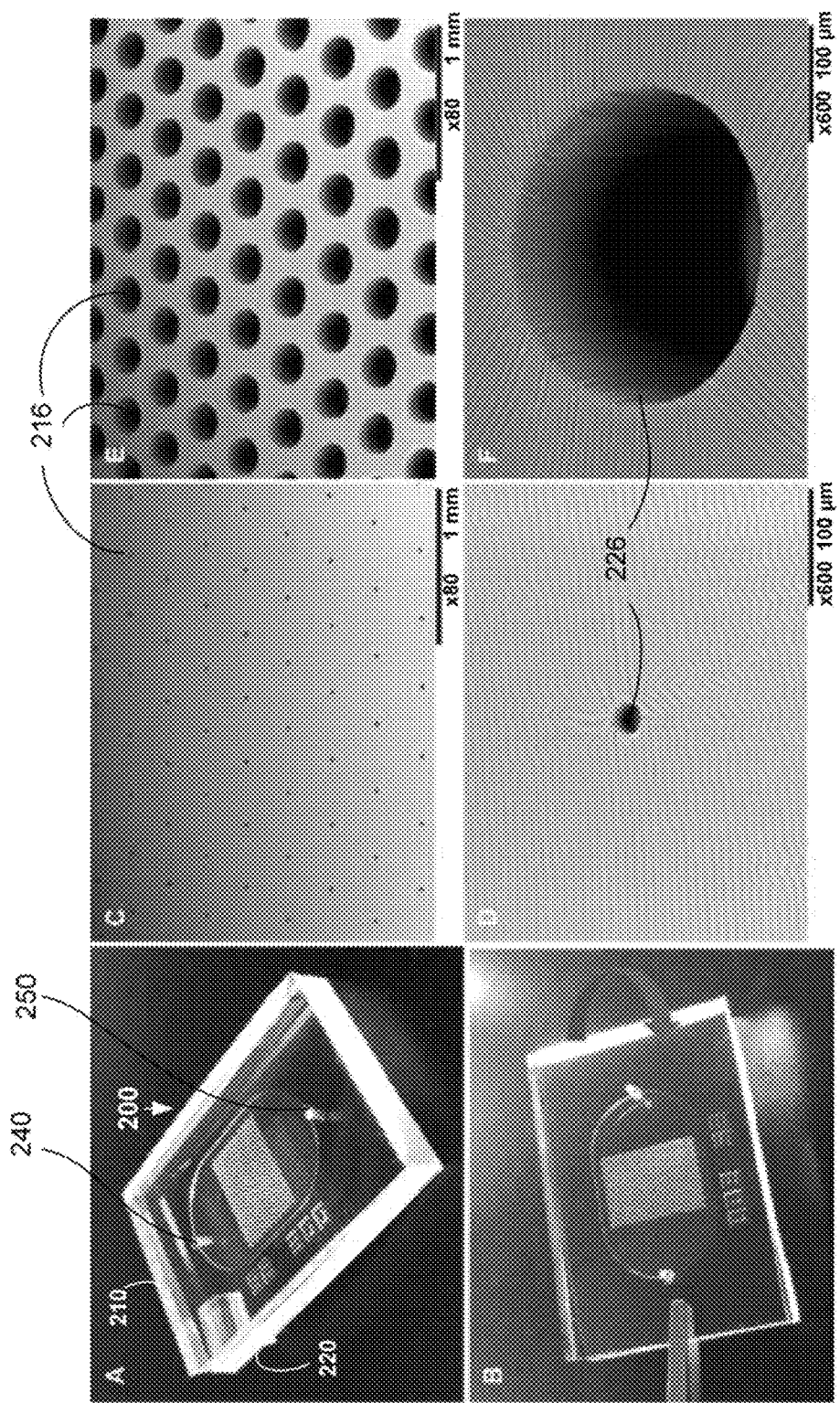
FIG. 1 shows photographs and SEM images of a dual-well (DW) device. (A) A top view showing a DW device in PDMS comprising two sets of microwell arrays, in which the set with the culture wells is on the top and the set with the capture wells at the bottom. The DW device may be made of any types of materials, including plastic materials such as polydimethylsiloxane (PDMS), polymethyl methacrylate (PMMA), polycarbonate (PC), and the like. (B) The DW device of (A) is in the process of being flipped over to transfer single cells in capture-wells to culture-wells. (C) SEM image of capture-wells viewed from the well side. (D) an enlarge view of a capture well of (C) 25 μm in diameter and 30±1 μm in depth. (E) SEM image of culture-wells viewed from the well side. (F) an enlarge view of a culture well from (E) 285 μm in diameter and 300±15 μm in depth.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around". "about" or "approximately" can be inferred if not expressly stated.

As used herein, the term "each well of the capture microwells" shall mean "each microwell of the capture microwells", and the term "each well of the culture microwells" shall mean "each microwell of the culture microwells".

As used herein, when a number or a range is recited, ordinary skill in the art understand it intends to encompass an appropriate, reasonable range for the particular field related to the invention.

By from 10 μm to 5 mm it meant that all integer unit amounts within the range are specifically disclosed as part of the invention. Thus, 10, 11, 12 . . . 4997, 4998, 4999, and 5000 μm unit amounts are included as embodiments of this invention.

By 0.5 μm to 1 mm it meant that all decimal unit amounts within the range are specifically disclosed as part of the invention. Thus, 0.5, 0.6, 07 . . . 998, 999, and 1000 μm unit amounts are included as embodiments of this invention.

By 10 μm to 1 cm it meant that all integer unit amounts within the range are specifically disclosed as part of the invention. Thus, 10, 11, 12 μm . . . 9997, 9998, 9999, and 10000 μm unit amounts are included as embodiments of this invention.

By 300 μm to 2 cm it meant that all integer unit amounts within the range are specifically disclosed as part of the invention. Thus, 300, 301, 302 μm . . . 19997, 19998, 19999, and 20000 μm unit amounts are included as embodiments of this invention.

By 5 μm to 3 mm it meant that all integer unit amounts within the range are specifically disclosed as part of the invention. Thus, 5, 6, 7 . . . 2997, 2998, 2999, and 3000 μm unit amounts are included as embodiments of this invention.

A biological microfluidic chip may be referred as a "biochip".

Abbreviations: Adenocarcinomic human alveolar basal epithelial cells (A549); scanning electron microscope (SEM).

Examples

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Device Design and Fabrication

The DW microfluidic devices were fabricated with polydimethylsiloxane (PDMS) using soft lithography techniques. Briefly, negative photoresist (SU-8, MicroChem, Newton, Mass. USA) was photolithographically patterned on silicon wafers to create masters. The height of the SU-8 features was measured using a scanning laser profilometer (VK-X 100, KEYENCE, Japan). The masters were then used as molds, on which Sylgard 184 (Dow corning, USA) PDMS pre-polymer mixed with its crosslinker at 10:1 ratio was poured and allowed to cure in a conventional oven at 65° C. for 3 hours. The cured PDMS replicas were peeled off from the molds. A puncher with 1.00 mm inner-diameter (HARRIS UNI-CORE™, Ted Pella, USA) was used to punch inlet holes for the fluidic channel of the PDMS device. After a brief oxygen plasma treatment, the PDMS replicas were aligned, brought into contact and placed in an oven at 65° C. for 24 hours to achieve permanent bonding between the PDMS replicas. See Lin et al. "A microfluidic dual-well device for highthroughput single-cell capture and culture" *Lab Chip.* 2015, 15, 2928-2938, which is herein incorporated by reference in its entirety.

A microfluidic device 200 is illustrated in FIGS. 1A, 2A, 12A-D. The dual-well device 200 comprises: (a) a first substrate 219, having a first end 210a, a second end 210b opposite to the first end 210a, and a culture microwell forming portion 210e with a thickness of t1 located between the two ends 210a, 210b, each end having a first surface 212 and a second surface 213 and a thickness of T1, the culture microwell forming portion 210c having a first surface 212 and a second surface 214 opposite to the first surface 212, wherein the thickness T1 of each end of the first substrate is greater than the thickness t1 of the culture microwell forming portion; (b) a plurality of culture microwells 216, each microwell having a diameter of w1 and a depth of d1, extending from the second surface 214 toward the first surface 212 of the culture microwell forming portion 219e; (c) a second substrate 220 with a thickness of t2, having a first surface 222 and a second surface 224 opposite to the first surface 222 of the second substrate 229, the second substrate having a first end 220a, a second end 220b opposite to the first end 220a, and a capture microwell forming portion 220c located between the two ends 220a. 220b of the second substrate 220, the two ends of the second substrate 220 being respectively bounded to the two ends of the first substrate 210 with its second surface 224 facing toward the second surface 214 of the first substrate 210 at a distance of h; (d) a plurality of capture microwells 226, each microwell having a diameter of w2 and a depth of d2, extending from the second surface 224 toward the first surface 222 of the second substrate 229, wherein the capture microwells 226 are in alignment with the culture microwells 216 so that each microwell 226 is corresponding to one culture microwell 216 and the projected area of each capture microwell 226 is within the projected area of the corresponding culture well 216, wherein the diameter w2 of each capture microwell 226 is smaller than the diameter w1 of each culture microwells 216; (e) a microfluidic channel 230 with a length of l (FIG. 12B), a width of w3 (not shown) and a height of h, formed between the two second surfaces of culture and capture microwell forming portions; (f) a microfluidic inlet port 240 defining an opening in the first surface of the substrate; (g) a microfluidic outlet port 250 defining an opening in the first surface of the substrate, opposite to the microfluidic inlet port 240; and wherein the microfluidic channel is in fluidic connections with the culture microwells, the capture microwells, and the inlet and outlet ports. The length l of the microfluidic channel 230 is defined as the distance between the inlet 240 and outlet 250 ports (FIG. 12B). The width w3 of the microfluidic channel 230 is dependent on the number of the arrays of the culture and capture microwells.

FIGS. 12A-D are schematic drawings illustrating a dual-well (DW) device 200. (A) a cross section view showing the first substrate 210 and the second substrate 220 are separate. (B) a cross section view showing the first substrate 210 and the second substrate 220 are assembled and bonded together. (C) a top view illustrating two culture microwells and two capture microwells. The diameters of the culture and capture microwells are w1, and w2, respectively. Two culture microwells are spaced apart at a distance of b1, and two capture microwells are spaced apart at a distance of b2. (D) a cross section view showing culture and capture microwells and microfluidic channel. The width and depth of a culture well is w1 and d1, respectively. The distance between the two culture well is b1 and the distance between the two capture well is b2. The thicknesses of culture microwell forming portion and capture microwell forming portion are t1 and t2, respectively. The distance between the second surfaces 224, 214 of the capture and culture microwell forming portions is h, which is also the height of the microfluidic channel 230. The length and width of the area encompassing two capture and two culture microwells are L and W, respectively.

The aforementioned parameters may be as follows: w1 ranging from 10 μm to 5 mm; d1 ranging from 10 μm to 5 mm, w2 ranging from 0.5 μm to 1 mm, and d2 ranging from 0.5 μm to 1 mm; b1 ranging from 10 μm to 1 cm; t1 and t2 ranging from 300 μm to 2 cm; h ranging from 5 μm to 3 mm. The area of the rectangle, enclosing two capture and culture microwells and denoted by the width W and the length L, ranging from 300 μm² to 900 mm². The design layout is such that one capture well is aligned vertically to a corresponding culture well. The capture well is positioned within the margins of the culture well. The shape of the culture and capture wells with widths of w1 and w2 includes, but is not limited to the, a circular shape as described herein. The spatial distribution of multiple culture wells relative to each other to form an array can be of any geometric pattern including the parallel distribution described herein.

DW Device Preparation for Single-Cell Capture

Prior to cell experiment, the DW devices were filled with deionized water and soaked in a deionized water-filled container in a desiccator to remove air-bubbles in the microchannel. Subsequently, the degassed DW devices were exposed UV light to sterilize for 30 minutes. To prevent immediate cell adhesion to the PDMS surface, 5% BSA (Bovine serum albumin, Bersing Technology. Taiwan) in 1×PBS was injected into microfluidic channel and incubated at 37° C. for 30 minutes.

Cell Culture and Maintenance

KT98 cells derived from FIB-TAg transgenic mouse brain were used as a cell model in this study. In routine maintenance, KT98 cells were cultured in DMEM/F12 medium (Gibco, USA) with 10% fetal bovine serum (Hyclone Thermo, USA) and 1% anti-biotics (Glutamine-Penicillin-Streptomycin, Biowest, France) at 37° C. and 5% $CO_2$ in a humidified incubator. Cancer cell lines—human lung cancer A549 and melanoma MDA-MB-435—were maintained in DMEM basal medium (Gibco, USA) with 10% fetal bovine serum (FBS, Biowest, France) and 1% anti-biotics. The cell cultures were passaged using a recombinant enzyme ACCUMAX™ (Innovative cell technology, USA) under the manufacture's standard protocol at 70-80% confluence.

Single-Cell Capture and Culture

Prior to each cell-capture experiment, the cells were prestained with a membrane dye (DilCl2(3), BD Biosciences, USA) for 20 minutes for easy-identification of the cells in the DW device. For each single-cell capture experiment, 200 μL of KT98 cells at 2.2-2.5×10⁶ cells/mL concentration (4.4-5×10⁵ cells) was loaded to a 200 μL plastic pipette tip followed by inserting the tip to the device inlet hole to manually inject the cells into the microfluidic channel of the DW device. This operation step can quickly load cells into the microchannel to cover the area of capture-wells. A syringe run by a syringe pump (Harvard Apparatus, Harvard Bioscience, USA) was then connected to the inlet of the DW device via a Teflon tubing (poly(tetrafluorethylene), inner dia.: 0.51 mm, outer dia.: 0.82 mm, Ever Sharp Technology, Inc., Taiwan) to drive 20 μL of the cell culture medium into the device at 3 μL/min. During this step, the cells in the microchannel moved slowly and could settle into the captured-wells by gravitational force. Subsequently, the uncaptured cells were washed away from the device by using 300 μL of the cell culture medium run at different flow rates of 200, 400, 600 and 800 μL/min. Finally, the inlet and outlet holes were sealed with plugs, and the device was flipped upside down to transfer the captured-cells to the culture-wells by gravitational force (FIGS. 1B, and 2A, black arrows). The device was then placed in a standard cell culture incubator at 37° C. and 5% $CO_2$ for 6-7 days.

KT98 Cell Differentiation in DW Devices

Stem cell differentiation in the DW devices was achieved by replacing the culture medium with a differentiation medium (NeuroCult™ Differentiation Kit, STEMCELL Technologies, Canada) 1 day after seeding KT98 cells in 485 μm-diameter culture-wells using the following steps: 1) the plugs in the inlet and outlet holes were removed. 2) A differentiation medium-loaded syringe was connected to the inlet hole via Teflon tubing. 3) A syringe pump was used to inject the differentiation medium into the microchannel of the DW device at a slow flow rate of 1.8 mL hr-1.4) The inlet and outlet holes were resealed with the plugs and the device was placed in a cell culture incubator in which the cells were cultured for 7 days. Then, the cells were fixed with 4% paraformaldehyde (Alfa Aesar, USA) for 15 minutes at room temperature, washed three times with 1×PBS, permeabilized with 0.25% Triton X-100 (Sigma, USA) in 1×PBS for 10 minutes and washed three times again with 1×PBS. After blocking nonspecific binding with 1% BSA in PBST (PBS+ 0.1% Tween-20), the cells were incubated with microtubule-associated protein 2 (MAP2. MAB378, Millipore, USA) antibody in a refrigerator at 4° C. overnight. Subsequently, the cells were incubated with FITC-conjugated secondary antibody for 1 hour at room temperature. All cells were stained with DAP1 to implement counter staining.

A549 Clonal Culture for EGF Promoted Colony Formation Assay in DW Devices

In the EGF promoted colony formation assay, 200 μL of A549 cells at a concentration of 2.2-2.5×106 cells per mL was injected into the DW device manually and allowed to settle for 2 min, followed by injecting DMEM with 20% FBS and 1% antibiotics into the microchannel immediately to wash off excess cells in the channel at a flow rate of 600 μL min⁻¹ for 30 s. Subsequently, the inlet and outlet holes were sealed and the device was flipped upside down to obtain a single cell in a culture-well. The device was then placed in a humidified incubator at 37° C. with 5% CO2 as described above. After 1 day of culture, one of the device (for the control experiment) was injected with 300 µL of DMEM containing 10% FBS and 1% antibiotics to replace the original medium. The other device (for the EGF treatment experiment) was injected with 300 µL of DMEM containing 10% FBS, 1% antibiotics and 200 ng mL-1 epithelial growth factor (EGF, PeproTech, USA) to replace the original medium. For both devices, the medium was replaced with fresh medium every 3 days. After 7 days of culture, the cells were imaged to assess the colony forming efficiency. Colonies with cell numbers higher than 15 cells in a culture-well were scored as cell colonies.

Cell Imaging

All cell images were obtained using an inverted microscope (Nikon Ti-E inverted fluorescence microscope, Japan) with an attached charge-coupled device (Retiga-4000DC, QImaging, Canada) and control software (NIS-Elements AR, Nikon, Japan).

Statistical Analyses

Figure 3:
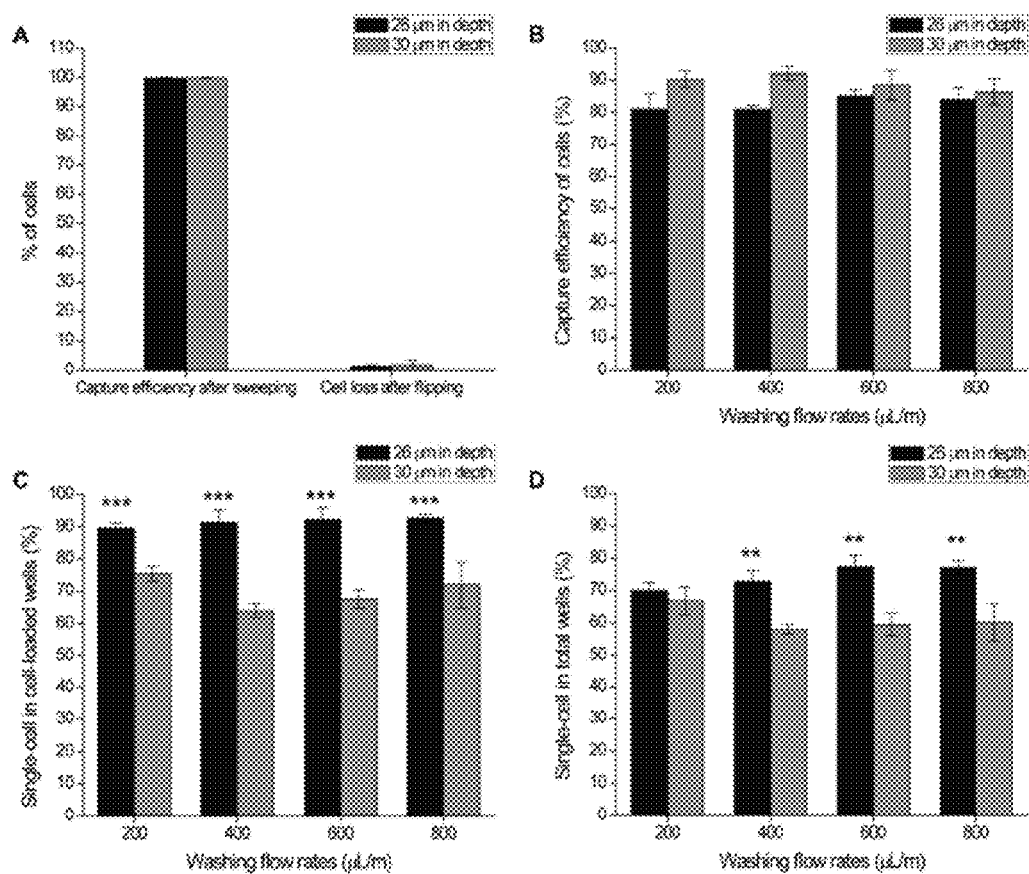
FIG. 3 shows KT98 cell loading efficiency after different operation steps in the DW device with 26 and 30 μm-deep capture-wells. (A) Efficiency of cell capture in capture-wells after sweeping reached 99.9%, and the cell loss after transferring the captured cells from capture-wells to culture-wells was less than 2% for both capture-well depths. (B) Cell capture efficiency in 30 μm-deep capture-wells (90.39%, 92.13%, 88.51% and 86.42%) was higher than that in 26 μm-deep capture-wells (80.97%, 80.94%, 85.16% and 83.97%) after washing at flow rates of 200, 400, 600 and 800 μL min$^{-1}$. (C) Frequency of single-cell events in cell-loaded culture-wells. The single-cell events of 26 μm-deep capture-wells were significantly higher than those of 30 µm-deep capture-wells at the four flow rates. (D) Frequency of single-cell events in total culture-wells. The single-cell events of 26 µm-deep capture-wells were also higher than those of 30 µm-deep capture-wells. Note that the highest single-cell event in total culture-wells (77%) was achieved in 26 µm-deep capture-wells with 600 µL min$^{-1}$ washing flow rate. Each experiment was performed in triplicate.
Figure 4:
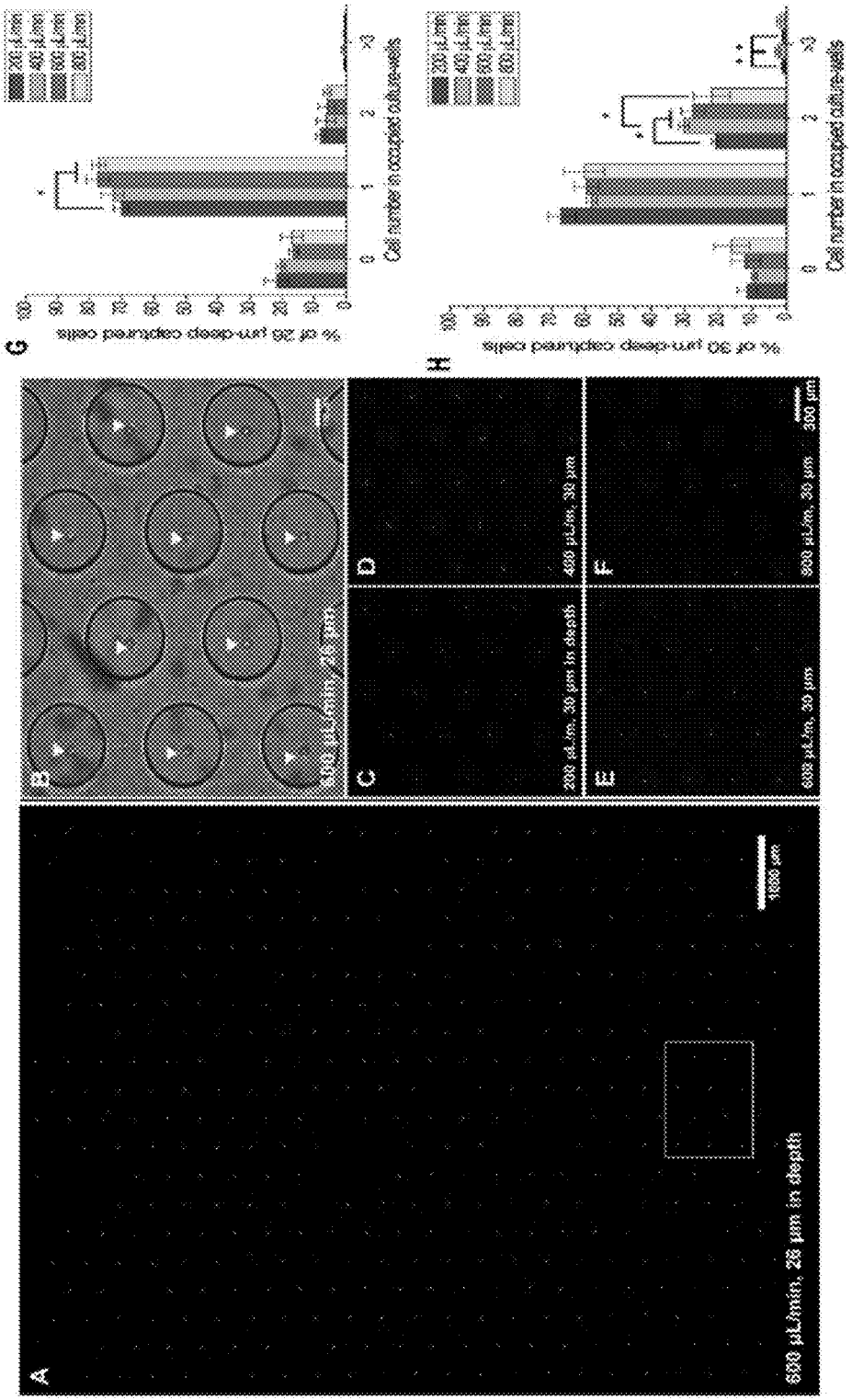
FIG. 4 shows representative images of cells and cell number in cell-occupied culture-wells after flipping the device (with 26 and 30 µm-deep capture-wells). (A) A stitched image containing all 470 culture-wells (with 600 µL/min washing flow rate). Scale bar: 1000 µm. (B) Enlarged overlapped images from the rectangular area of stitched image showing each culture-well containing one single cell. Arrowheads indicate the single-cells in culture-wells. (C-F) Representative images from experiments using four different washing flow rates of 200, 400, 600 and 800 µL/min. Higher frequency of 2 or >3 cell-occupied culture-wells were shown in the results of experiment using the 400 µL/min washing flow rate. (G-H) Cell number in cell-occupied culture-wells at the four washing flow rates. The single-cell ratio was higher using 600 or 800 µL/min washing flow rates (77.31% and 77.09%, respectively), and lowest using 200 µL/min washing flow rates (70.07%) with 26 µm-deep capture-wells. (H) The highest ratio of single events in total culture-wells (66.81%) was obtained by using the 200 µL/min washing flow rate with 30 µm-deep capture-wells.
Figure 5:
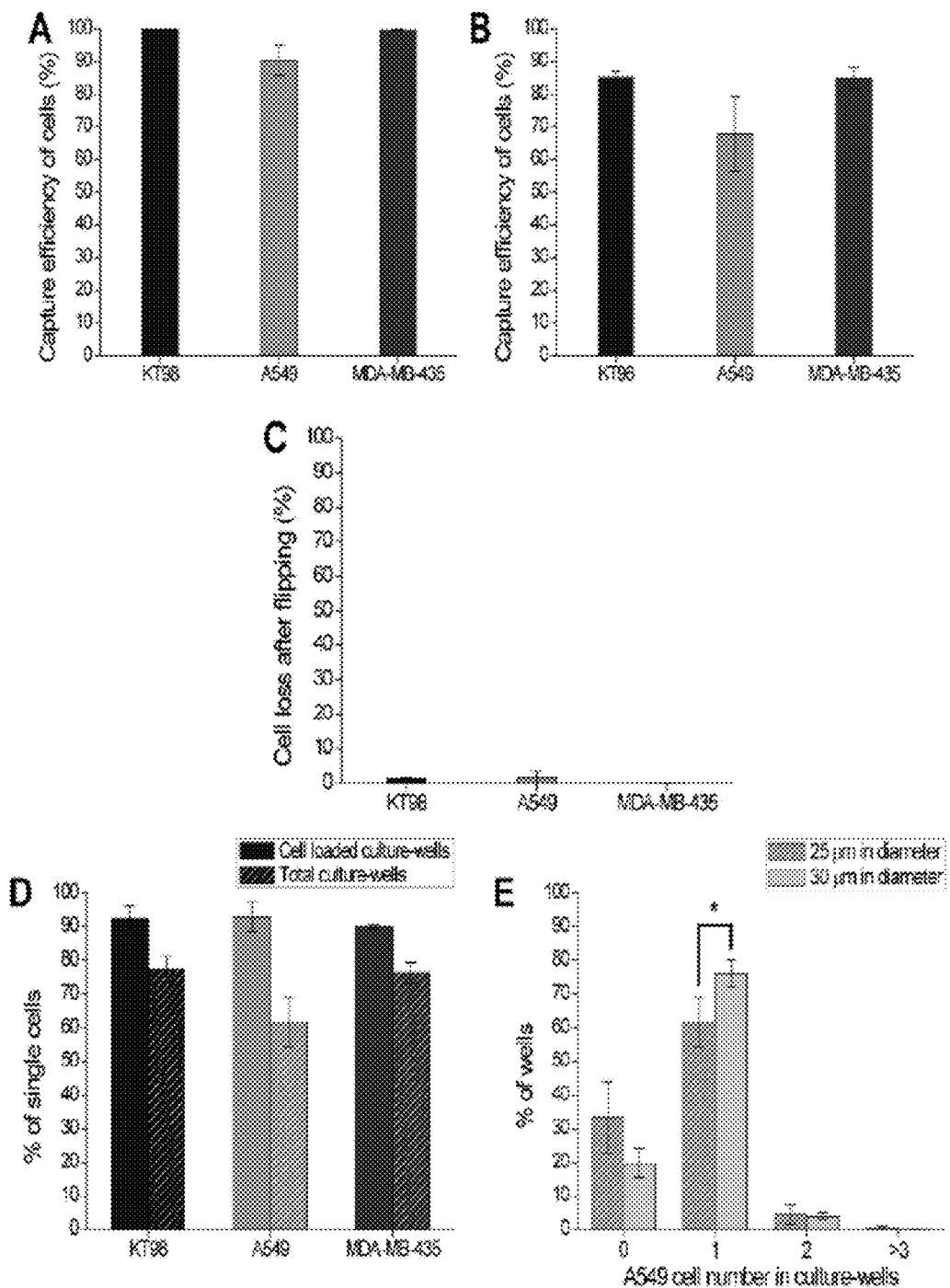
FIG. 5 shows KT98, A549 and MDA-MB-435 cell loading efficiency with 600 µL/min washing flow rate and 26 µm deep capture-wells. (A) Capture efficiency of KT98 and MDA-MB-435 cells were higher than 99%, but that of A549 was 90.21% after sweeping. (B) Efficiency of KT98, A549 and MDA-MB-435 cells captured in capture-wells after washing at the flow rate of 600 µL/min. (C) Cell loss was less than 2% for all the three cell types after flipping the device. (D) The single-cell ratio in total culture-wells (slash bar) of KT98, A549 and MDA-MB-435 cells were 77.31%, 61.63% and 76.31%, respectively. (E) The single-cell capture efficiency of A549 was significantly increased from 61.63% to 76.03% when the depth of the capture-well was increased to 30 µm. Each experiment was performed in triplicate.

All experiments were performed in triplicate or quadruplicate, and data are presented as mean±standard deviation (SD). One-way analysis of variance (ANOVA) and Student's t-test were used for the comparison of each group. In FIG. 3 to 5, the statistical significance was indicated with asterisks used to denote statistical significance at $*p<0.05$, $p<0.01$ and $*p<0.001$ in the FIGures.

Transferring and Releasing of Cell Colonies from Culture Well

Here, we present a novel method to retrieve selected cells from microfabricated devices. This method retrieve the cells by removing a porting of the device which is physically attached to the cells of interest. This method does not require the use of flow, or capillary or micropipette, and can keep the retrieved cells viable for downstream cell analysis and culture.

Briefly, after culture, cells transferring and releasing were performed by punching out cell-containing plugs from the PDMS device. The bonding area between the two substrates (capture microwell substrate and culture microwell substrate) was cut away carefully to separate the PDMS culture microwell structure (i.e., the first substrate) from the PDMS capture well structure (i.e., the second substrate). The PDMS culture microwell structure was then placed on a flat surface with the wells/openings facing upward (i.e., the first surface of the first substrate is placed at the bottom and the second surface with the culture microwells is facing upward).

Figure 8:
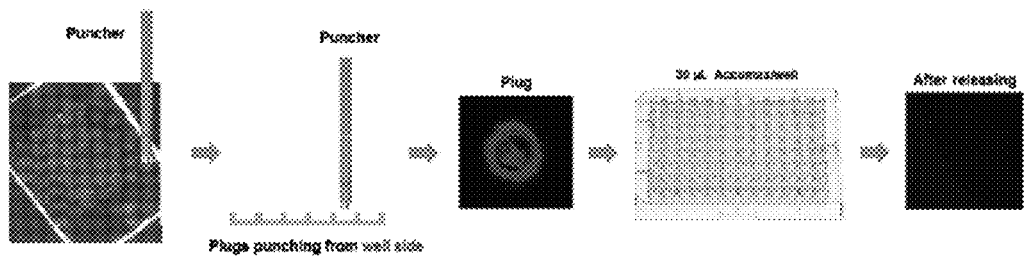
FIG. 8 shows cell transferring and releasing from PDMS DW device and growth in a 96-well plate. (A) Operation steps for transferring a single-cell colony from a PDMS culture microwell to a well plate and releasing of the colony from the PDMS. (B) A graph showing the colony growth efficiency of various samples in the well plate after the colony transfer from the PDMS DW device to a well plate. (C) A microphotograph of a well plate illustrating a released cell (white arrowhead) and a PDMS plug (black arrowhead) in a well plate.
Figure 8:
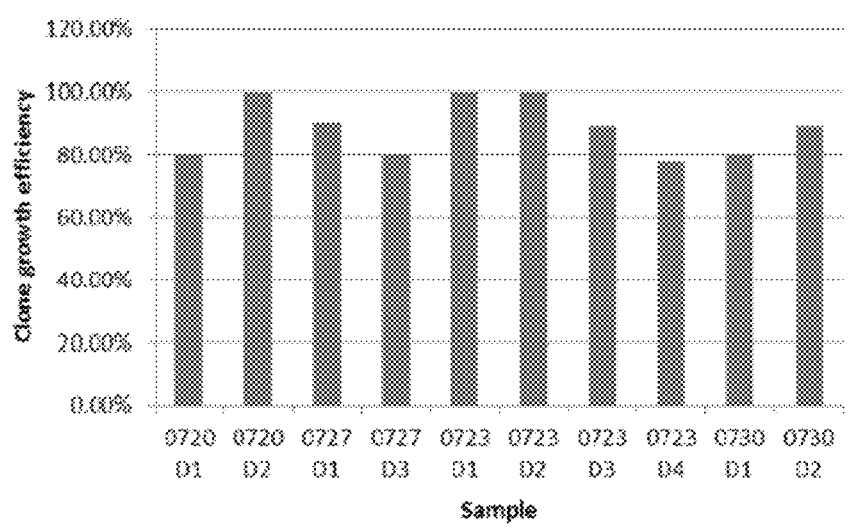
Figure 8:
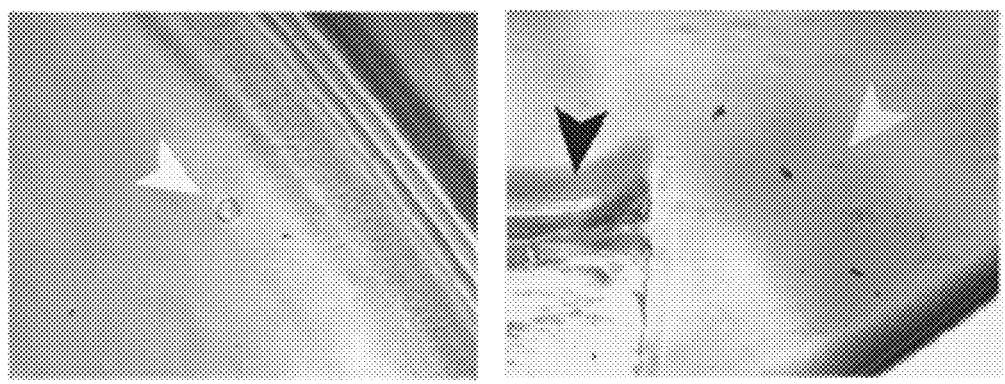

The cell transferring process is illustrated in FIG. 8A. First, the locations of the target colonies were identified after examining all wells of the culture device. Second, the PDMS device containing the culture wells soaked in a culture medium-filled container. Third, each culture-well containing target cells was punched out from the device with a tissue puncher and subsequently transferred to a 96-well plate well containing 30 µL of a dissociation solution (ACCUMAX™). To punch out the cells, the tissue puncher was directed precisely toward the culture wells containing the target cells of interest, and one microwell at a time to punch out from the first PDMS substrate as a plug (or a micro-cylinder) that contains cell colonies. Each plug containing the cell colonies was then transferred to the 96-well plate containing the dissociation solutionACCUMAX™. Fourth, after all the target cells had been transferred, the 96 well-plate was kept in a biohood at room temperature for 10 min, followed by agitating the 96-well plate with a well-plate shaker for 1 min at room temperature. Finally, 150 µL of culture medium was added into each well and the 96 well-plate was placed into a standard cell culture incubator at 37° C. and 5% CO2. After 1 day of culture, the original culture medium was replaced with new culture medium to completely remove ACCUMAX™ in the cell culture medium.

Results

Device Design and Operation

Figure 2:
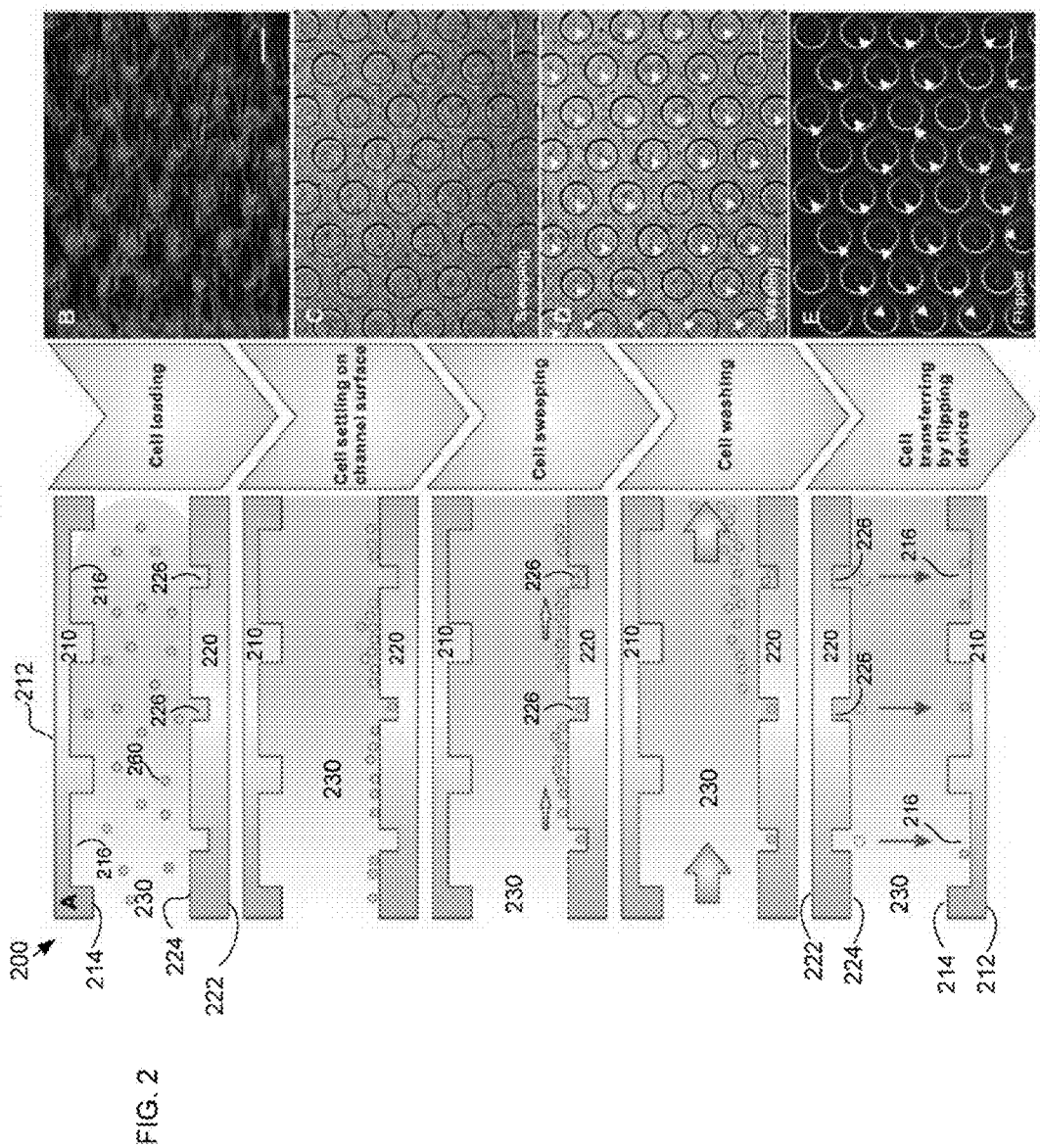
FIG. 2 is a schematic illustration showing the DW device's operation procedure. (A) a flow diagram showing a cross-section of a DW device and operation steps including cell loading, sweeping, washing and transferring. (B) A top view of a long exposure image (90 seconds) taken in the sweeping step, showing that 89.87% of the channel floor area was covered by the trajectories of fluorescently (DiI membrane dye) labeled KT98 cells. (C) A top view image showing that cell capture efficiency in capture-wells is enhanced by moving cells with a slow flow. (D) A top view image showing that uncaptured cells are removed from the microchannel by washing. (E) A top view image showing that cells in capture-wells are transferred to culture-wells by flipping the device. White arrowheads points to an individual single cell located in a culture well. Scale bar: 300 μm.

As shown in FIG. 1, the dual-well device 200 comprising a microchannel with two sets of microwell arrays 210, 220 (each set contains 470 wells in an area of $10.65 \times 7.7$ mm$^2$) on its ceiling and floor. One set of the microwell arrays 220 has a size of each microwell being close to that of a single cell, is used to trap single cells at high efficiencies. We have successfully adapted this method to achieve high-efficiency single-cell trapping in the DW device 200. The two sets of microwell arrays 210, 220 were designed in different sizes with each microwell in one set 220 (called capture wells or cell-capture well) being 25 µm in diameter and 26 or 30±1 µm in depth (0.013 nL for each 26 µm well, 0.015 nL for each 30 µm well) and in the other set 210 (called culture wells or cell culture well) being 285 or 485 µm in diameter and 300±15 µm in depth (~20 nL for each 285 µm well, ~55 nL for each 485 µm well).

Referring to FIG. 2A, the microchannel 230 height between the two sets 210, 220 of microwell arrays was 200 µm, resulting in a total volume of 60 µL for the DW device. The footprint (which is the area enclosing the microfluidic channel, i.e., channel length l×channel width w3) of the dual-well device is $12.75 \times 20.25$ mm$^2$. The positions of the capture- and culture-wells are arranged in a way that from the top-view angle, the position of each cell-capture well 226 is located at the center of a cell culture well 216. The operation steps of the DW device are as follows: First, a cell 260 suspension is injected into the microfluidic channel 230 with a manual pipette while the device 200 is placed at its "capture position" in which the capture-wells 226 are on the channel's floor and the culture-wells 216 are on the ceiling. FIG. 2B shows microfluidic channel 230 being loaded with a cell suspension. After the cells settles on the channel surface (the second surface 224 of the second substrate 220), a tubing connected to a culture medium-loaded syringe is inserted into the microchannel's inlet 240 to inject a medium to "sweep" the cells 260 at a slow flow rate controlled by a syringe pump. This step increases the probability of cell docking in the capture-wells 226 (FIG. 2C). The DW device could also be alternatively operated with this sweeping step skipped. Subsequently, the flow rate is increased to wash away the uncaptured cells (FIG. 2D). Finally, the inlet and outlet holes 240, 250 are plugged after removing the tubing, and the DW device 200 is gently flipped to its "culture position" in which the capture-wells 220 are on the channel's ceiling and the culture-wells 210 are on the floor, allowing the captured cells to fall off from the capture-wells to the culture-wells by gravity (FIG. 2E). The loading procedure takes about 8-9 minutes to perform and once flipped, the device can be immediately placed in a humidified container (e.g., a Petri dish) and in a conventional cell culture incubator for subsequent cell culture and experiments. The DW device can be straightforwardly operated with conventional syringe pumps, tissue culture incubators and microscopes making it highly adaptable to biological laboratories.

Single-Cell Capture Efficiency of DW Device with KT98 Cells

For a cell to settle into a capture microwell, the projected area of the cell needs to overlap with that of the capture microwell. Therefore putting more cells in the microchannel could in theory increase the efficiency of microwell cell capture by increasing the probability of having cells on top of the microwells. However increasing cell density could also increase cell clustering during cell suspension preparation and device operation which decreases single cell capture yield. To avoid using very high-density cell suspension while keeping cell capture at high efficiency, a cell "sweeping" procedure is used in our system. We found that using 20 µL of medium driven at 3 µL/min was fast enough to move the cells in the microchannel, but slow enough to allow the cells to settle into the capture-wells. Using a KT98 cell suspension with a density of 2.2-2.5×106 cells per mL, we observed minimal cell clustering and more than 99% of the capture-wells were occupied by cells (FIGS. 2C and 3A). We also tested the effect of washing flow rates on cell retention in the capture-wells and found that only a portion of the capture-wells (26 µm in depth) lost their initially loaded cells with no significant difference (ranging from 81-85%) among the four tested flow rates after the washing step (FIG. 3B). However, the washing flow rates did have a prominent effect on the number of cells being captured in a capture-well as shown by the cell loading results in culture-wells after flipping the device; the highest single-cell loading efficiency in the culture-wells was obtained with washing flow rates of 600 and 800 µL min$^{-1}$ (FIG. 4G), indicating that more capture wells were loaded with one cell using the 600 or 800 µL min$^{-1}$ flow rate (note that the flipping step only resulted in less than 2% cell loss (FIG. 3A)). Altogether, our results showed that with the current microwell dimensions, multiple single cells could stack in a capture-well and be washed out from the well depending on the washing flow rate used, and the highest single-cell loading efficiency in the culture-wells of KT98 cells (77.31±3.70%) could be obtained by using the 600 µL min$^{-1}$ washing flow rate with the 26 µm deep capture-wells. Additionally, to understand whether the single-cell capture ratio could be affected by the depth of the capture-wells, we conducted a single-cell capture efficiency test with another device which has deeper capture-wells (30 µm). The results showed that the cell capture efficiency after sweeping was not affected by the depth difference between the shallow (26 µm) and deep (30 µm) capture-wells; both reached a very high efficiency (>99%) after sweeping (FIG. 3A). However, for the washing step, lower cell losses were obtained with the deep wells at the four flow rates (86.42-92.13% cell retention) than those with the shallow wells (80.94-85.16%, FIG. 3B). On the other hand, the single-cell ratio in the cell-loaded culture wells was decreased (from 89-92% to 64-75%, FIGS. 3C and 4D) when the capture-well depth was increased (from 26 to 30 µm), resulting in the reduction of the single-cell ratio in the total culture-wells (from 70-71% to 58-66%, FIG. 3D). The highest single-cell ratio in the total culture-wells (66.81±4.15%) was obtained by using the 200 µL min-1 washing flow rate with 30 µm-deep capture-wells.

Single-Cell Capture Efficiency of Different Cell Types

To investigate the applicability of the DW device to other cell types, two additional cell line cells—human lung cancer A549 and melanoma MDA-MB-435—were tested with the DW device using 3 µL/min sweeping flow rate and 600 µL/min washing flow rate with the 26 µm deep capture-wells according to the optimal KT98 single-cell loading results as described above. The results showed that the ratio of cell-occupied capture wells after sweeping and washing is cell-type dependent (ranged from 67.80±11.38%-85.16±1.91%, FIG. 5B). Cell loss after the flipping step was low for all cell types of KT98, A549 and MDA-MB-435 (all less than 2%. FIG. 5C). Interestingly, most of the cell-loaded culture-wells contained only a single cell in each well for all the three cell types (89.89%-92.98%). All together our result showed that the DW device had a good single-cell loading efficiency in culture-well for KT98 and MDA-MB-435 (more than 76%, FIG. 5D), except for A549 (61.63±7.47%). To improve the single-cell loading efficiency in the culture-well of different sizes of cells, we used the same depth but wide (from 25 µm to 30 µm in diameter) capture-well for cell trapping. Results showed a significant increment of single-cells loading efficiency (61.63% to 76.03%, FIG. 5E) was obtained using the A549 cell model. This result indicated that the efficiency of single-cell loaded in the culture-well relied on the relationship between the sizes of cells and capture-wells.

Figure 6:
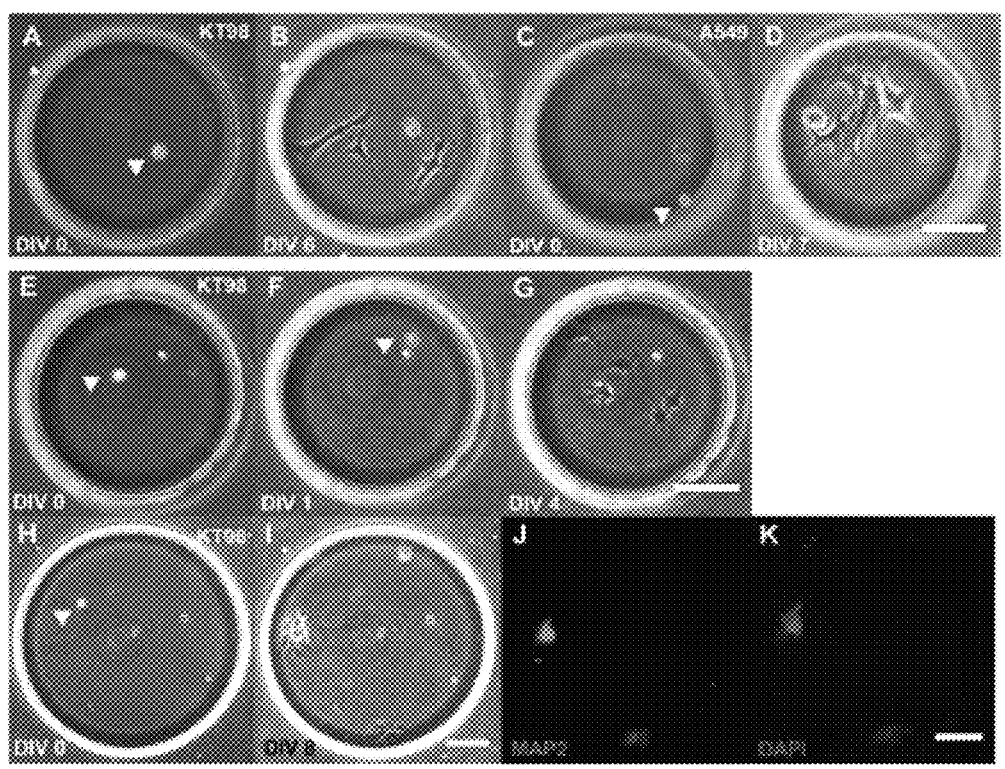
FIG. 6 shows cell proliferation and neuronal lineage differentiation of neural stem cells in culture-wells for 6-8 days. (A) Cell membrane dye (DiI) staining facilitated cell identification shown in the phase and fluorescence overlapped image. (B) Proliferated KT98 colony in a culture-well after 6 days of in vitro culture. (C) DiI staining image showing a single A549 cell loaded into a culture-well. (D) Proliferated A549 colony which exhibited normal cell morphology in a culture-well after 7 days of in vitro culture. (E-G) Phase images showing the proliferation and differentiation of a single KT98 cell in a culture-well (285 µm in diameter). The cell divided into 6 cells and exhibited neurite morphology after culture in a differentiation medium for three days. (H-I) A single KT98 cell in a culture-well (485 µm in diameter) showing the proliferation and differentiation processes from DIV 0 to DIV 8. (J) The differentiated KT98 cells expressed neuronal lineage marker MAP2 after 7 days of differentiation. (K) Cell nuclei were stained with DAP1 as the counterstain. Arrowheads indicate single cells in culture-wells. Scale bar: 100 µm.

Single-Cell Proliferation and Stem Cell Differentiation in the Microwells of DW Device The applicability of the DW device to cell proliferation was demonstrated with KT98 and A549 cells. The enlarged culture-wells provided sufficient surface area for the cells to attach and spread as well as adequate medium volume for cell proliferation for up to one week. Using culture-wells of 285 µm diameter (~20 nL), single KT98 and A549 cells were able to divide into 6-8 cells from a single cell in the microwell and form a colony (FIGS. 6A-D) after 6-7 days of culture in the device. On the other hand, the large culture-wells and medium exchangeable feature of the DW device allowed us to demonstrate its utility in stem cell differentiation which requires long cell culture times ranging from 7-16 days for embryonic stem cells and 7-21 days for neural stem cells. As shown in FIG. 6E-G, after replacing the culture medium with a differentiation medium in the DW device one day after cell loading, a single KT98 cell in a culture-well (285 µm in diameter) divided into 6 cells and exhibited neurite morphology specific to neuronal cells. As shown in FIG. 6H-K, successful differentiation of KT98 from a single KT98 cell was also verified by immunocytochemistry staining of microtubule-associated protein 2 (MAP2)—a neuronal lineage protein marker which is involved in the microtubule assembly essential for neuritogenesis.

Dual-Well Device for Small Molecule Testing on Colony Formation Assay

Figure 7:
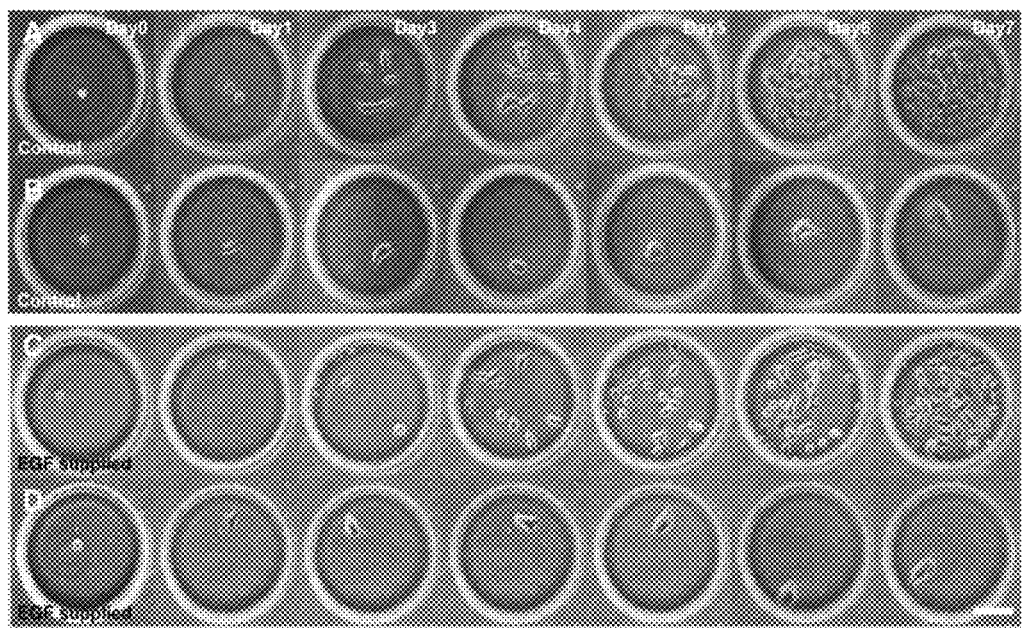
FIG. 7 shows epithelial growth factor (EGF) promoted colony formation ratio of A549 single cells after 7 days of culture. (A) A cell colony grew from an A549 single cell and (B) a single cell did not proliferate but survived after 7 days of culture in a control medium. (C) An A549 single cell proliferated to form a colony. (ID) An undivided single cell survived for 7 days after culture in the EGF supplied medium. Scale bar: 100 µm. (E) The A549 single cells showed a heterogeneous cell number distribution after being cultured in the control or EGF supplied medium for 7 days. (F) The colony forming efficiency of A549 cells with an EGF supplied medium was higher than that of the A549 cells cultured with a control medium. Each experiment was performed in triplicate.
Figure 7:
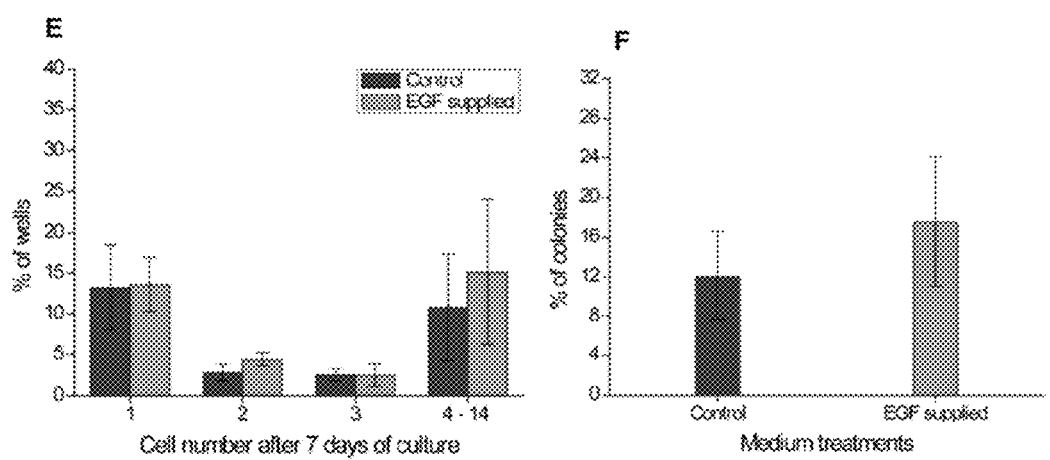

Due to its high single-cell capture efficiency and large space of culture wells, the DW device represents an attractive tool for in vitro single-cell colony formation assays in which the growth of individual cells is analyzed. For cancer research, single-cell colony formation assay can be used to test the effect of drugs or small molecules on cancer cell proliferation. We used A549 cells to test their colony formation abilities in response to EGF, which is widely used to study epidermal growth factor receptor-mediated signaling for cancer treatment. FIG. 7F shows that a higher colony forming efficiency (17.56%) was obtained from cells in EGF-supplied medium compared to that (12.10%) treated with control medium. Our result confirmed that the EGF-receptor expressing A549 cancer cells proliferate more rapidly when exposed to EGF. The portability and transparency of the DW device allowed the cells in the device to be conveniently analyzed with a conventional microscope during cell culture experiments (FIGS. 7A-D). This assay also highlights the strength of the DW device by showing its applicability to studying cellular heterogeneity at the single-cell level, as we were able to measure the differences in cell survival and proliferation rate among the tested individual A549 cells. Only 40-55% of the loaded cells survived after 7 days of culture, and those live cells exhibited different growth patterns and rates (e.g., 1 cell (13%), 2 cells (2.8-4.3%), 3 cells (2.5%), and 4-14 cells (10-15%), FIG. 7E). These results demonstrated that the DW device can be used for single-cell colony formation assays and is advantageous because a large number of individual cell colonies grown in a small area can be straightforwardly measured with a conventional microscope.

Figure 9:
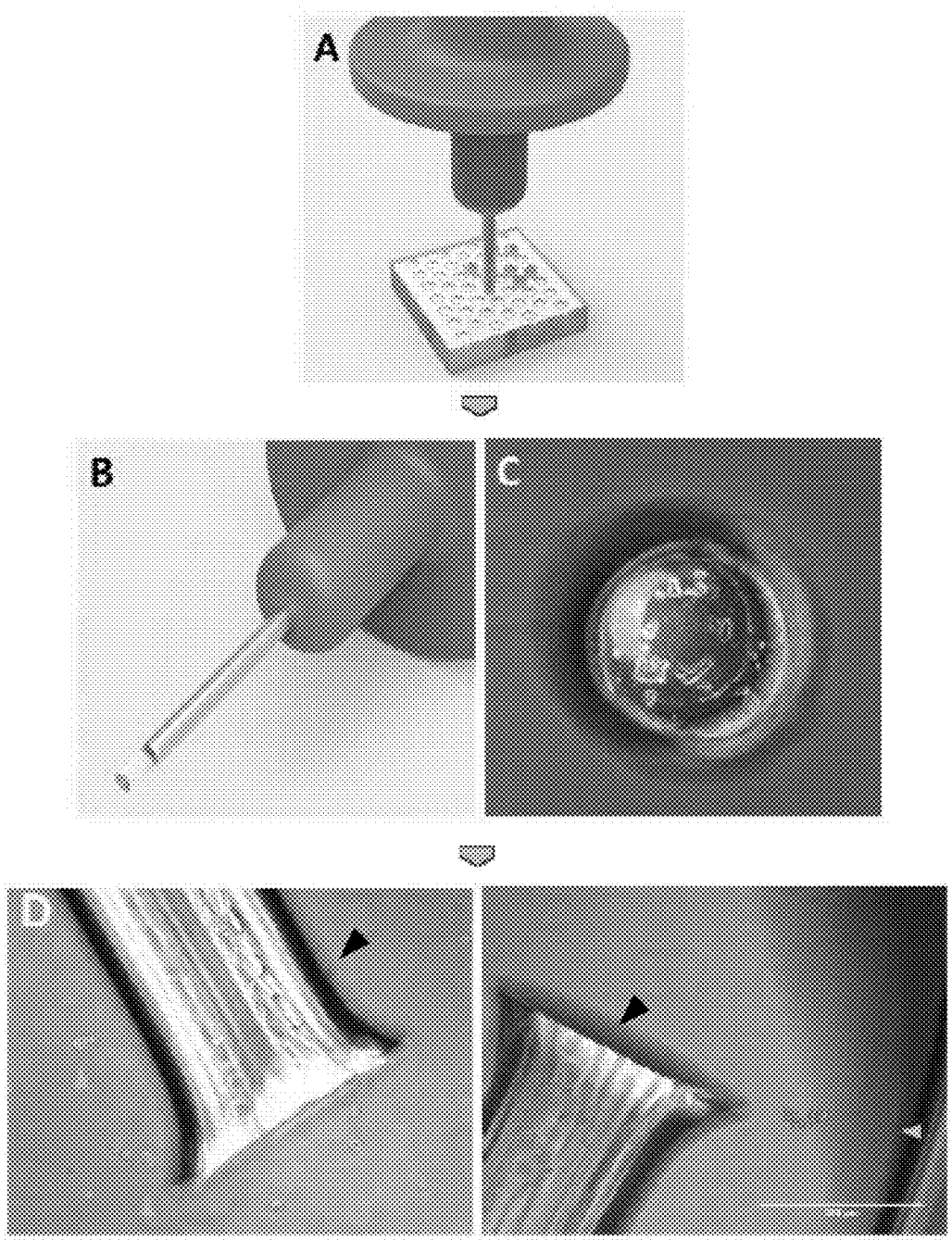
FIG. 9 shows operation steps for transferring cells from the PDMS device to a well plate. (A & 8) Harvesting cells from the culture well using a puncher. (C) The punched out plug containing cells. (D) The released cells (yellow arrowhead) and the PDMS plugs (black arrowhead) in a well of a 96 well-plate.

Target Cell Harvest and Release in 96 Well-Plates after Cell Transfer from PDMS Device After culturing cells on the multi-well PDMS, the target wells were punched out using a puncher (FIGS. 8A and 9A). The punched plugs contained the cells (FIGS. 8A, 9B and C). The plugs were then transferred to a 96 well-plate well containing 30 µL of ACCUMAX™ solution, one plug per well. The cells were released from the plug into the well of the plate after the ACCUMAX™ treatment (FIGS. 8A, 8C, 9C, and 9D).

Cell Growth in 96 Well-Plates after Cell Transfer from PDMS Device

Figure 10:
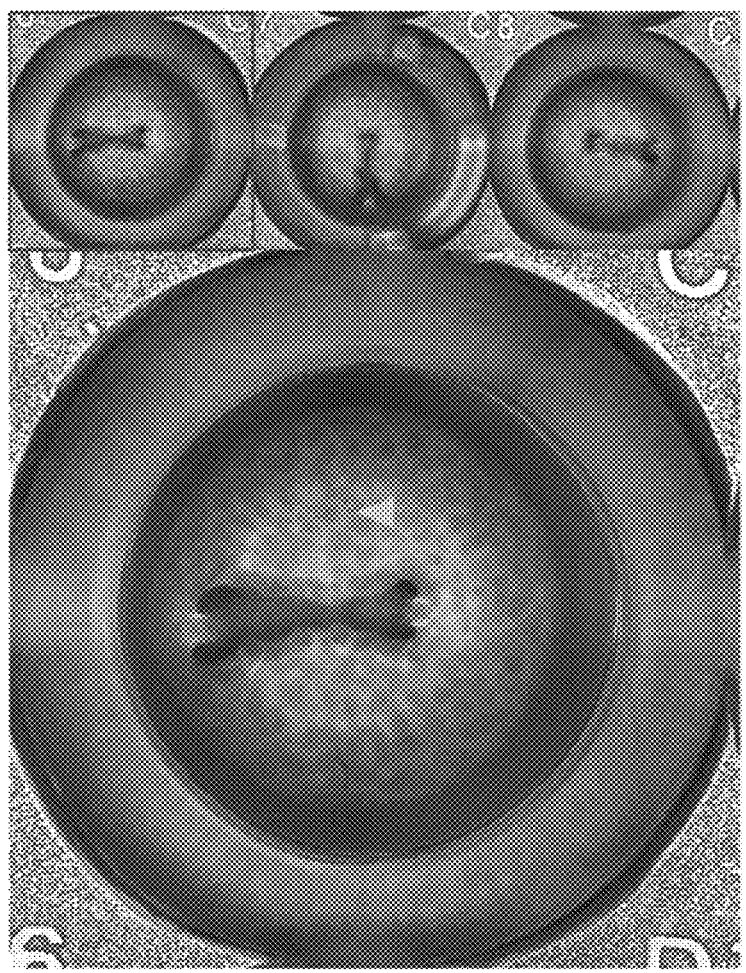
FIG. 10 are microphotographs showing the attached and proliferated cells (yellow arrowhead) and the PDMS plugs (black arrowhead) in a well of a 96 well-plate after 7 days.
Figure 11:
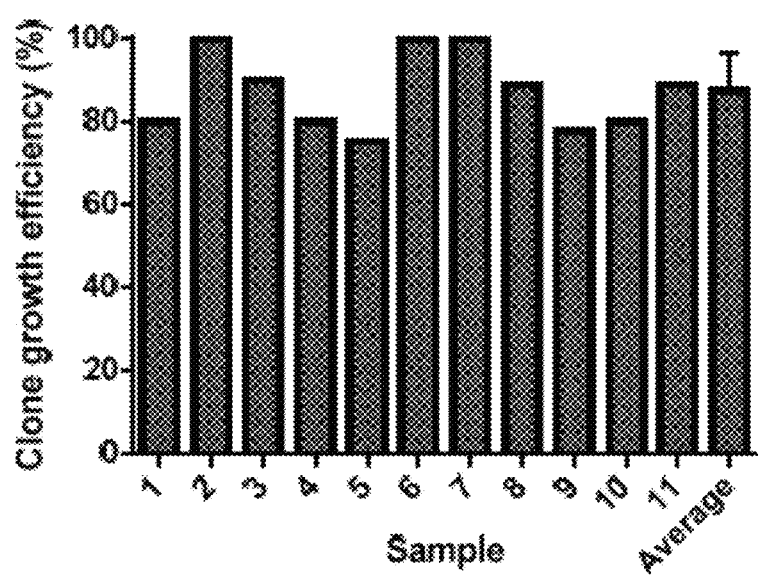
FIG. 11 is a graph showing cell growth efficiency in the 96 well-plate after transferring from the PDMS device.

FIG. 10 shows cell growth in a 96 well-plate after cell transfer from the PDMS device. The cells successfully attached onto the well plate and proliferated. To understand how the cells would grow in a 96 well-plate after the cell transfer from the PDMS DW device, we analyzed the number of cells in each well of the 96-well plate for 10 days. Most of the transferred cells continued to proliferate; the efficiency is shown in FIGS. 8B and 11.

In conclusion, we have presented a new microfluidic single cell-culture device which utilizes a dual-well concept to increase single cell loading efficiency in microwells whose sizes are significantly larger than that of a single cell. We have also demonstrated the use of the DW device in cell differentiation and colony formation assay experiments with cancer and stem cells. We believe that the ability of our approach to allow for high-efficiency loading of single cells in large microwells may be useful for a broad range of applications where on-device culture and analysis of single cells are required.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A microfluidic dual-well device comprising:
    (a) a first substrate, having a first end, a second end opposite to the first end, and a culture microwell forming portion with a thickness of t1 located between the two ends, each end having a first surface and a second surface and a thickness of T1, the culture microwell forming portion having a first surface and a second surface opposite to the first surface wherein the thickness T1 of each end of the first substrate is greater than the thickness t1 of the culture microwell forming portion;
    (b) a plurality of culture microwells, each microwell having a diameter of w1 and a depth of d1, extending from the second surface toward the first surface of the culture microwell forming portion;
    (c) a second substrate with a thickness of t2, having a first surface and a second surface opposite to the first surface of the second substrate, the second substrate having a first end, a second end opposite to the first end, and a capture microwell forming portion located between the two ends of the second substrate, the two ends of the second substrate being respectively bounded to the two ends of the first substrate with its second surface facing toward the second surface of the first substrate at a distance of h;
    (d) a plurality of capture microwells, each microwell having a diameter of w2 and a depth of d2, extending from the second surface toward the first surface of the second substrate, wherein the capture microwells are in alignment with the culture microwells so that each microwell is corresponding to one culture microwell and the projected area of each capture microwell is within the projected area of the corresponding culture well, wherein the diameter w2 of each capture microwell is smaller than the diameter w1 of each culture microwells;
    (e) a microfluidic channel with a length of l, a width of w3 and a height of h, formed between the two second surfaces of culture and capture microwell forming portions;
    (f) a microfluidic inlet port defining an opening in the first surface of the first substrate; and
    (g) a microfluidic outlet port defining an opening in the first surface of the first substrate, opposite to the microfluidic inlet port;
    wherein the microfluidic channel is in fluidic connections with the culture microwells, the capture microwells, and the inlet and outlet ports.

2. The microfluidic dual-well device of claim 1, wherein the surfaces of the microfluidic channel are coated with albumin.

3. The microfluidic dual-well device of claim 1, wherein the surfaces of the microfluidic channel are coated with bovine serum albumin.

4. The microfluidic dual-well device of claim 1, further comprising a fitting adapted to seal the inlet and outlet ports.

5. The microfluidic dual-well device of claim 1, further comprising cells suspended in a medium within the microfluidic channel, wherein the size of each well of the capture microwells is adapted to capture a single cell from the cells within the microfluidic channel.

6. The microfluidic dual-well device of claim 1, further comprising single cells in the capture microwells.

7. The microfluidic dual-well device of claim 6, wherein the inlet and outlet ports are sealed liquid-tight.

8. The microfluidic dual-well device of claim 1, further comprising single cells in the culture microwells.

9. The microfluidic dual-well device of claim 8, wherein the inlet and outlet ports are sealed liquid-tight.

10. The microfluidic dual-well device of claim 8, wherein more than one well of the culture microwells comprise a single cell, and each well of the culture microwells has space adapted for the single cell to attach, grow and/or proliferate.

11. The microfluidic dual-well device of claim 8, wherein more than one well of the culture microwells comprise a single-cell colony.

12. The microfluidic dual-well device of claim 1, further comprising a tubing adapted to connect to the inlet and/or outlet ports.

13. The microfluidic dual-well device of claim 1, wherein each well of the capture microwells has a depth of no greater than 30 μm.

14. The microfluidic dual-well device of claim 13, wherein each well of the capture microwells has a depth of less than 30 μm.

15. The microfluidic dual-well device of claim 1, wherein the first and second substrates are made of a material selected from the group consisting of polydimethylsiloxane (PDMS), polymethyl methacrylate (PMMA), and polycarbonate (PC).

16. A method of capturing and transferring a single cell or a single cell colony for culture, comprising:
   (a) providing the microfluidic dual-well device of claim 2 with the first substrate on the top and the second substrate at the bottom;
   (b) loading cells suspended in a culture medium into the microfluidic channel via the inlet port;
   (c) allowing the cells in the microfluidic channel to settle into and captured by the capture microwells and/or to settle on the second surface of the second substrate;
   (d) washing away uncaptured cells by delivering a washing medium into the microfluidic channel via the inlet port; and
   (e) flipping over the microfluidic dual-well device to place the first substrate at the bottom and the second substrate on the top to transfer the captured cells from the capture microwells to the culture microwells for culture.

17. The method of claim 16, wherein the first and second substrates are made of polydimethylsiloxane (PDMS).

18. The method of claim 16, wherein step (c) further comprises the step of:
   sweeping the cells settled on the second surface of the second substrate by delivering the culture medium into the microfluidic channel to increase the probability of cell-docking in the capture microwells, wherein the flow rate of the medium during the sweeping step is slower than that during the washing step.

* * * * *